United States Patent [19]
Borden et al.

[11] Patent Number: 5,461,077
[45] Date of Patent: Oct. 24, 1995

[54] USE OF PERBROMIDES TO CONTROL DISEASES IN PLANTS

[75] Inventors: Dennis M. Borden, West Lafayette; Nicolai A. Favstritsky, Lafayette, both of Ind.

[73] Assignee: Great Lakes Chemical Corp., West Lafayette, Ind.

[21] Appl. No.: 141,179

[22] Filed: Oct. 21, 1993

[51] Int. Cl.$^6$ ............................................ A01N 33/12
[52] U.S. Cl. ............................................ 514/642; 514/643
[58] Field of Search ...................... 504/345; 514/642, 514/643

[56] References Cited

U.S. PATENT DOCUMENTS

| | | | |
|---|---|---|---|
| 3,068,144 | 12/1962 | Gilbert | 167/33 |
| 3,342,581 | 9/1967 | Woodward et al. | 71/65 |
| 3,390,178 | 6/1968 | Hyatt | 260/567.6 |
| 3,412,021 | 11/1968 | Paterson | 210/62 |
| 3,542,538 | 11/1970 | Jung et al. | 71/76 |
| 3,564,046 | 2/1971 | Newhall | 260/501.15 |
| 4,058,618 | 11/1977 | Ovchinnikov et al. | 424/273 R |
| 4,167,832 | 9/1979 | Zetterquist et al. | 47/1 R |
| 4,198,423 | 4/1980 | Rentzea et al. | 424/273 R |
| 4,454,133 | 6/1984 | Berke et al. | 424/267 |
| 4,655,815 | 4/1987 | Jakubowski | 71/67 |
| 4,886,915 | 12/1989 | Favstritsky | 564/503 |
| 4,898,975 | 2/1990 | Favstritsky | 564/2 |
| 4,925,866 | 5/1990 | Smith | 514/389 |
| 4,935,153 | 6/1990 | Favstritsky et al. | 210/755 |
| 4,966,716 | 10/1990 | Favstritsky et al. | 210/755 |

OTHER PUBLICATIONS

"Phytotoxicity of Bromine in Plants," Chemical Literature Report, Great Lakes Chemical Corporation (Sep. 10, 1991).

*Primary Examiner*—Gary E. Hollinden
*Assistant Examiner*—Brian M. Burn
*Attorney, Agent, or Firm*—Woodard, Emhardt, Naughton, Moriarty & McNett

[57] ABSTRACT

A method for controlling diseases in plants, comprising applying to the roots or leaves of the plant a water-soluble, mono- or di-substituted ammonium perhalide of the formula:

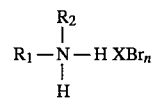

where $R_1$ and $R_2$ are independently hydrogen, hydroxyethyl, alkyl, cyclic alkyl, (alpha, omega)-alkyl, alkyl ether, polyether, heterocyclic ring-substituted alkyl, and halogenated alkyl; X is chlorine, bromine or iodine; n is 2 to 6; and only one of $R_1$ and $R_2$ is hydrogen.

In another aspect of the invention, plant seeds are disinfected by applying the water-soluble, mono- or di-substituted ammonium perhalide to the seeds.

24 Claims, No Drawings

USE OF PERBROMIDES TO CONTROL DISEASES IN PLANTS

FIELD OF THE INVENTION

The present invention relates generally to the control of diseases in plants, and more particularly to the use of organic ammonium perhalides to control plant diseases.

BACKGROUND TO THE INVENTION

Diseases in plants may be caused by environmental factors or by living organisms. Environmental factors such as drought, excessive moisture, lack of nutrition, improper temperature, etc., are generally controlled by proper management techniques, while disease-causing organisms such as fungi and bacteria may be somewhat more difficult to control. There are literally thousands of such organisms, and they may inhabit and infect the soil or roots, as well as the visible plant. Because of the significant economic roles of both nutritive and decorative plants, the effective treatment of plant diseases caused by fungal and other organisms is an important goal which has long demanded considerable attention.

A variety of agents are known to control diseases in plants. For example, copper-containing and lime-sulfur sprays have been used to control fungus and bacterial diseases, particularly on fruit trees, berry bushes and roses. Similarly, bleaches and other chlorine-based compounds have been used in certain circumstances, although somewhat less commonly as their harmful side effects have become more fully appreciated. Also, organic fungicides such as Captan (N-trichloromethylthio tetrahydrophthalimide), Arasan (tetramethyl-thiuram disulfide), Semesan (hydroxmercurichlorophenol) and Spergon (tetrachlorobenxoquinone) have been used with limited success.

Many of the products available for plant disease control have substantial limitations. For example, treatment with copper is generally not preferred, in part due to its phytotoxicity. Also, many agents provide an unsatisfactory spectrum of activity due to the resistance which develops in the target pathogens. In addition, some potential disease control agents are effective only in a narrow pH range, and are therefore not suitable for general agricultural use. Finally, some prior art agents, such as bleach or various quaternary ammonium compounds, are toxic not only to the target pathogen, but to humans and animals as well.

In addition to health hazards from the toxicity of the disease control agents of the prior art, such agents also typically involve other dangers such as explosiveness, corrosivity, etc. Also, conventional chlorine-based compounds exhibit instability in the presence of organic matter, and tend to form chloramines in the presence of ammonia—thereby producing residual compounds which undesirably persist in the environment.

A need therefore exists for improved methods and agents for the control of diseases in plants. In particular, a need exists for agents which provide effective control of diseases in plants without being toxic to either the plant or the consumer of the plant or its fruit. A need further exists for agents which may be used to treat plant seeds to ward off diseases which may infest the seeds. The present invention addresses these needs.

SUMMARY OF THE INVENTION

Briefly describing one aspect of the present invention, there is provided a method for controlling plant diseases, comprising applying to the roots or leaves of the plant a water-soluble, mono- or di-substituted ammonium perhalide of the formula:

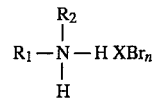

where $R_1$ and $R_2$ are independently hydrogen, hydroxyethyl, alkyl, cyclic alkyl, (alpha, omega)-alkyl, alkyl ether, polyether, heterocyclic ring-substituted alkyl, polyoxyalkylene or halogenated alkyl; X is chlorine, bromine or iodine; n is 2 to 6; and only one of $R_1$ and $R_2$ is hydrogen.

In another aspect of the invention, plant seeds are disinfected by applying the water-soluble, mono- or di-substituted ammonium perhalide to the seeds.

One object of the present invention is to provide a method of controlling diseases in plants without harming the plants.

Another object of the present invention is to provide a method of controlling diseases in plants which is non-toxic to humans and animals.

A third object of the present invention is to provide a method of controlling diseases in plants which is environmentally benign.

Further objects of the present invention will be apparent from the following description.

DESCRIPTION OF THE PREFERRED EMBODIMENT

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the described embodiments, and such further applications of the principles of the invention as illustrated herein, being contemplated as would normally occur to one skilled in the art to which the invention pertains.

The present invention relates to the discovery that ammonium perhalides, their metabolites and residuals, can be used for the effective control of diseases in higher order plants without risk of injury to the plants. More particularly, it has been found that aqueous solutions of ammonium perhalide may be formulated in a wide range of concentrations effective to kill various plant diseases, yet low enough not to harm the plants. Importantly, the ammonium perhalides of the present invention are both safe and effective regardless of whether the compound is applied in solid or liquid form.

As indicated above, one aspect of the present invention provides a method for controlling diseases in higher order plants by applying ammonium perhalides to the roots or leaves of the plants. The water soluble mono- and di-substituted ammonium perhalides of the invention are compounds of the formula:

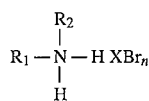

where $R_1$ and $R_2$ are independently hydrogen, hydroxyethyl, alkyl, cyclic alkyl, (alpha, omega)-alkyl, alkyl ether, polyether, heterocyclic ring-substituted alkyl, polyoxyalkylene or halogenated alkyl; X is chlorine, bromine or iodine; n is 2 to 6; and only one of $R_1$ and $R_2$ is hydrogen. These perhalide compounds are generally prepared by reacting the corresponding mono- or di-substituted ammonium hydrohalide salt with bromine as outlined below. A more complete discussion of the synthesis and development of the compounds of the present invention can be found in U.S. Pat. Nos. 4,886,915, 4,898,975, 4,935,153 and 4,966,716, all to Favstritsky et al., which are incorporated herein by reference.

Briefly describing the preparation of the perhalides of the present invention, the compounds can be prepared by first reacting the corresponding amines with hydrogen halide (Equation 1), followed by the addition of bromine (Equation 2):

$$R_1R_2NH + HX \rightarrow R_1R_2NH_2X \quad (1)$$

$$R_1R_2NH_2X + Br_2 \rightarrow R_1R_2NH_2XBr_2 \quad (2)$$

Most conveniently, an aqueous solution of lower alkyl- or dialkyl-ammonium perbromides can be prepared by reacting the readily available and inexpensive aqueous 48% hydrobromic acid with neat amine. The resulting aqueous amine hydrobromic salt is then readily converted to the perbromide by the addition of bromine. A simple one-pot procedure produces aqueous solutions of perbromides with exceedingly high bromine content.

Another method of preparing the same compound consists of first dissolving the bromine in hydrobromic acid, followed by the addition of the neat amine:

$$HBr + Br_2 \rightarrow HBr_3 \quad (3)$$

$$HBr_3 + R_1R_2NH \rightarrow R_1R_2NH_2XBr_2 \quad (4)$$

Still another method for the preparation of these compounds, especially if higher bromine content in the solution is desired, consists of reacting a more concentrated hydrobromic acid with amine, followed by bromine addition. Alternatively, the corresponding aqueous solution of the amine hydrobromide can be concentrated by evaporating water, followed by the addition of an appropriate amount of bromine.

Finally, anhydrous perbromides can also be easily prepared by gently heating the dry amine hydrobromide salt with bromine. Analogous procedures may be employed to produce the chlorine and iodine containing perhalides of this invention by employing the corresponding hydrogen halide in the foregoing reactions.

The perhalides of this invention include those containing additional bromine. The bromine content of these perhalides may be increased by adding more than one mole of bromine to the substituted-ammonium hydrobromide, yielding a higher perbrominated salt, as illustrated by Equation 5:

$$R_1R_2NH_2Br + 2Br_2 \rightarrow R_1R_2NH_2Br_5 \quad (5)$$

Although four or more moles of bromine can be added to the aqueous amine hydrobromide, the solution, upon contact with excess water, releases elemental bromine. However, it is possible to prepare solutions of perbromides in which the bromine content approaches $R_1R_2NH_2Br_5$ but which do not release bromine upon contact with excess water.

As indicated, the compounds of the present invention include mono- and di-substituted perhalides wherein X may be chlorine, bromine or iodine. It is preferred, however, to employ compounds in which X is bromine, such as perbromides of the formula $R_1R_2NH_2$—$Br_3$.

Specific stable, water soluble perhalides useful with the method of the present invention include ethanolammonium perbromide, propylammonium perbromide, diethanolammonium perbromide, butylammonium perbromide, methyethanolammonium perbromide, ethylethanolammonium perbromide, hexylammonium perbromide, octylammonium perbromide, dipropylammonium perbromide, dibutylammonium perbromide, diethylammonium perbromide, 1,6-hexanediammonium perbromide, as well as the corresponding chloro and iodo-dibromides. Ethanolammonium perbromide has been most preferred in testing to date.

The ammonium perhalides are preferably provided as a solution in water. The concentration of ammonium perhalide in the solution should be at least about one part per million, and preferably at least about 10 ppm. As will be seen in the examples which follow, concentrations of about 25 ppm are required to control plant diseases in certain applications. Obviously, the maximum concentration of ammonium perhalide in the composition should not exceed the point at which the composition becomes phytotoxic. Under ordinary circumstances, the maximum concentration will not exceed about 200 ppm, at which concentration phytotoxicity is not observed.

Preferably, the ammonium perhalide is provided at a concentration of between about 10 ppm and about 50 ppm by weight in the treated water. The ammonium perhalide accordingly provides a concentration of between about 5 ppm and about 100 ppm bromine by weight in the treated water, preferably between about 5 ppm and about 25 ppm. The appropriate concentration for a particular application can be determined by one skilled in the art without undue experimentation.

The solubility and bromine content of the compounds depend on the bulk and nature of the substituents. The most preferred substituents are $R_1$=hydroxyethyl, $C_1$ to $C_8$ alkyl groups, and $R_2$=hydrogen, hydroxyethyl, or $C_1$ to $C_8$ alkyl groups. In general, the compounds of the present invention are highly soluble in water, and their application in aqueous solution is readily accomplished.

It has further been found that solid ammonium perhalides are not harmful to plants. Accordingly, the compositions of the present invention may be applied in solid form in plant environments, or indeed to the plants themselves, without risk of injury to plant systems or tissue.

Moreover, since ammonium perhalides are not believed to pose health dangers to humans at their recommended dilution level, ingestion of plants or parts thereof treated with such formulations presents no appreciable risk. If ingestion of even trace quantities of perhalide is to be avoided, the compositions of the present invention are readily washed off of plants or seeds. Finally, since ammonium perhalides are neither flammable nor typically stored in pressurized containers, they do not present dangers from explosion.

The ammonium perhalides of this invention also show greater stability in the presence of organic matter and effectiveness over a wider pH range than shown by typical chlorine disinfectants. Further, the ammonium perhalides of this invention do not tend to form chloramines in the presence of ammonia, and so to not form residual compounds which undesirably remain in the environment.

If desired, the shelf life of aqueous solutions of the compounds of this invention may be stabilized by increasing the amount of ammonium hydrohalide in relation to bromine. More particularly, up to four moles of mono- or di-substituted ammonium hydrohalide salt may be admixed with one mole of bromine. Shelf life stability may also be increased by replacing part of the substituted ammonium hydrohalide salt with other stability enhancing salts such as alkali metal and ammonium bromides, especially equimolar amounts of ammonium bromide and sodium bromide. Preferably, the substituted ammonium hydrohalide salt and other stability enhancing salt, if any, are provided in a ratio of about 1 to 4 moles of salt to 1 mole of bromine.

Due to the selective toxicity of aqueous ammonium perhalide compositions, the compositions can be employed in a variety of applications wherein the composition contacts higher order plants. Accordingly, greenhouse surfaces susceptible to pathogenic microorganism development may be cleaned with a solution of ammonium perhalide without undue concern as to whether any of the solution incidentally contacts the plants growing in the greenhouse. Moreover, ammonium perhalide can be incorporated into irrigation water to control the growth of pathogenic microorganisms in the water, on the irrigation equipment, and on contiguous surfaces.

It has also been found that because of the selective phytotoxicity characteristic, ammonium perhalide can be incorporated into irrigation water or otherwise applied directly to plants, or to the growth medium in which plants are rooted, to control certain plant diseases without harming the plants. Also surprisingly, it has been discovered that treating growing plants with ammonium perhalide and then harvesting the plants, or their fruit or seeds, results in harvested plants, fruit or seeds that do not rot or spoil as early as do harvested untreated plants, or fruit or seeds from untreated plants. It further has been found that the benefit of delayed rotting or spoiling also can be achieved by applying ammonium perhalide composition directly to the harvested plants, fruit and seeds.

As for plants themselves, the cleaner water provided by this method is believed to deliver to the plants via the roots thereof fewer living microorganisms that could be deleterious to the plant. Moreover, the biocidal activity of the treated water delivered to the plant is believed to inhibit microorganism development in and on the plant, and so helps prevent or control certain plant diseases which could result from pathogenic microorganisms. Importantly, therefore, this method is effective to control diseases that otherwise spread quickly through the plants in a greenhouse. Despite such biocidal activity of water treated with ammonium perhalide, the plant itself is not harmed by the treated water.

As with greenhouse plants, crops or plants in an outdoor nursery may be irrigated with treated water. Ammonium perhalide may be incorporated anywhere in the water system as described above, and the plants irrigated with the treated water by any of several irrigation methods, such as spray irrigation, trickle or drip irrigation, mist or fog irrigation, sub-irrigation, ebb-and-flow irrigation, and hydroponics. As with the greenhouse irrigation methods, the treated water acts to control unwanted microorganisms from developing on the irrigation equipment, as well as in or on the plants and growth medium in which the plants are rooted. The treatment thereby helps prevent certain plant diseases arising from pathogenic microorganisms and controls the outbreak and spread of such diseases.

In an alternative embodiment of the method of the invention, solid ammonium perhalide may be placed on or in the ground near growing plants so that rain or irrigation water delivers the ammonium perhalide to the plant's roots or rhizosphere. Likewise, solid ammonium perhalide may be placed on or in the ground near implanted bulbs or seeds so that rain or irrigation water delivers the ammonium perhalide to the roots or rhizosphere of plants grown from the bulbs or seeds. Or, if desired, the plants, bulbs or seeds themselves may be treated by applying powder or granular ammonium perhalide or a slurry or solution of ammonium perhalide directly to the plants, bulbs or seeds before or after planting.

In still another alternative embodiment of the present invention, growing plants may be treated with the treated water or by foliar application of an ammonium perhalide powder, slurry or solution to inhibit the development of unwanted microorganisms and diseases on or in the fruit or seeds of the treated plants, and to delay rotting or spoiling of the plants, fruit or seeds even after harvesting. Significantly, the treatment process of this invention not only is harmless to the plants, but at the recommended dilution levels the ammonium perhalides are no more hazardous to humans than typically treated swimming pool water. Accordingly, the resulting low doses of ammonium perhalide in the harvested plants, fruits and seeds appear to pose no appreciable health hazards to humans consuming them.

Alternatively, or additionally, ammonium perhalide can be applied topically to plants, fruit or seeds after harvest to form a treatment solution. More particularly, the harvested plants, fruits or seeds can be sprayed or washed with the treatment solution, or the harvested plants, fruit or seeds can be dusted or coated with ammonium perhalide powder or an ammonium perhalide slurry. Regardless, the harvested plants, fruit and seeds are not harmed, nor are they believed to be toxic to humans. Disease-causing microorganism development in and on the harvested plants, fruit and seeds is, however, inhibited, and rotting and spoiling are delayed.

Reference will now be made to specific examples using the compositions described above. It is to be understood that the examples are provided to more completely describe preferred embodiments, and that no limitation to the scope of the invention is intended thereby.

EXAMPLE 1

Preparation of Perbromides

In a five liter, four-necked, round-bottom flask, immersed in an ice bath and equipped with a mechanical stirrer, reflux condenser, addition funnel and thermometer, HBr (48%) (1940 g/11.5 moles) is placed. Ethanolamine (703 g/11.5 moles) is slowly added at a rate such that the temperature does not exceed 50° C. to ensure minimal loss of HBr.

After the addition of the ethanolamine is complete, the reaction mixture (61.8% ethanolamine hydrobromide) is allowed to cool to room temperature. Then, bromine (1840 g/11.5 moles) is carefully added via the addition funnel, and the temperature is maintained below 50° C. The yield of the dark red aqueous ethanolammonium perbromide is 4483 g.

EXAMPLES 2–10

Examples 2 through 10 relate to the in vitro testing of ethanolammonium perbromide with respect to its efficacy in controlling fungi and bacteria. The test pathogens were cultured in appropriate media and were treated with varying amounts of ethanolammonium perbromide. For the bacterial tests, treatment was typically initiated several days after the inoculum start date. For the fungi tests, treatment was typically initiated several weeks after the inoculum start date. In all cases, pathogen counts were taken several days after treatment.

The results of the in vitro testing are shown in the Examples below.

EXAMPLE 2

In Vitro Test 1
Pathogen - *Pseudomonas cichorii* - P231
Culture medium - King's Medium B
Bacterial Counts After Treatment With
Ethanolammonium Perbromide

|  | Water Control | 1 ppm | 5 ppm | 10 ppm | 25 ppm |
|---|---|---|---|---|---|
|  | 21 | 0 | 0 | 0 | 0 |
|  | 18 | 0 | 0 | 0 | 0 |
|  | 14 | 0 | 0 | 0 | 0 |
|  | 33 | 0 | 0 | 0 | 0 |
|  | 25 | 0 | 0 | 0 | 0 |
| average | 22.2 | 0 | 0 | 0 | 0 |
| average % reduction | n/a* | 100 | 100 | 100 | 100 | n/a = not applicable

EXAMPLE 3

In Vitro Test 2
Pathogen - *Xanthomonas campestris* pv. *dieffenbachiae* - X186
Culture medium - Nutrient Agar
Bacterial Counts After Treatment With
Ethanolammonium Perbromide

|  | Water Control | 1 ppm | 5 ppm | 10 ppm | 25 ppm |
|---|---|---|---|---|---|
|  | 131 | 4 | 0 | 0 | 0 |
|  | 157 | 3 | 0 | 0 | 0 |
|  | 151 | 1 | 0 | 0 | 0 |
|  | 137 | 2 | 0 | 0 | 0 |
|  | 128 | 1 | 0 | 0 | 0 |
| average | 140.8 | 2.2 | 0 | 0 | 0 |
| average % reduction | n/a* | 99.98 | 100 | 100 | 100 | n/a = not applicable

EXAMPLE 4

In Vitro Test 3
Pathogen - *Erwinia chrysanthemi* - E11
Culture medium - Nutrient Agar
Bacterial Counts After Treatment With
Ethanolammonium Perbromide

|  | Water Control | 1 ppm | 5 ppm | 10 ppm | 25 ppm |
|---|---|---|---|---|---|
|  | 56 | 0 | 0 | 0 | 0 |
|  | 66 | 0 | 0 | 0 | 0 |
|  | 65 | 0 | 0 | 0 | 0 |
|  | 73 | 0 | 0 | 0 | 0 |
|  | 74 | 0 | 0 | 0 | 0 |
| average | 66.8 | 0 | 0 | 0 | 0 |
| average % reduction | n/a* | 100 | 100 | 100 | 100 |

-continued

In Vitro Test 3
Pathogen - *Erwinia chrysanthemi* - E11
Culture medium - Nutrient Agar
Bacterial Counts After Treatment With
Ethanolammonium Perbromide

| Water Control | 1 ppm | 5 ppm | 10 ppm | 25 ppm |
|---|---|---|---|---| n/a = not applicable

EXAMPLE 5

In Vitro Test 4
Pathogen - *Myrothecium roridum* - 87-160
Culture medium - Potato dextrose agar
Spore Counts After Treatment with
Ethanolammonium Perbromide

|  | Water Control | 1 ppm | 5 ppm | 10 ppm | 25 ppm |
|---|---|---|---|---|---|
|  | 135 | 143 | 7 | 0 | 0 |
|  | 125 | 195 | 12 | 0 | 0 |
|  | 166 | 158 | 6 | 0 | 0 |
|  | 157 | 168 | 7 | 0 | 0 |
|  | 174 | 202 | 18 | 0 | 0 |
| average | 151.4 | 173.2 | 10 | 0 | 0 |
| average % reduction | n/a* | 14.4 | 99.3 | 100 | 100 | n/a = not applicable

EXAMPLE 6

In Vitro Test 5
Pathogen - *Fusarium moniliforme* - 70
Culture medium - potato dextrose agar
Spore Counts After Treatment With
Ethanolammonium Perbromide

|  | Water Control | 1 ppm | 5 ppm | 10 ppm | 25 ppm |
|---|---|---|---|---|---|
|  | 66 | 45 | 0 | 0 | 0 |
|  | 70 | 32 | 0 | 0 | 0 |
|  | 62 | 57 | 0 | 0 | 0 |
|  | 58 | 43 | 0 | 0 | 0 |
|  | 85 | 35 | 0 | 0 | 0 |
| average | 68.2 | 42.4 | 0 | 0 | 0 |
| average % reduction | n/a* | 37.8 | 100 | 100 | 100 | n/a = not applicable

EXAMPLE 7

In Vitro Test 6
Pathogen - *Botrytis cinerea* - 92-5
Culture medium - potato dextrose agar
Spore Counts After Treatment With
Ethanolammonium Perbromide

|  | Water Control | 1 ppm | 5 ppm | 10 ppm | 25 ppm |
|---|---|---|---|---|---|
|  | 23 | 15 | 1 | 0 | 0 |
|  | 24 | 20 | 0 | 0 | 0 |
|  | 20 | 25 | 0 | 0 | 0 |

-continued

In Vitro Test 6
Pathogen - *Botrytis cinerea* - 92-5
Culture medium - potato dextrose agar
Spore Counts After Treatment With
Ethanolammonium Perbromide

|  | Water Control | 1 ppm | 5 ppm | 10 ppm | 25 ppm |
|---|---|---|---|---|---|
|  | 18 | 20 | 0 | 0 | 0 |
|  | 23 | 18 | 0 | 0 | 0 |
| average | 21.6 | 19.6 | 0.2 | 0 | 0 |
| average % reduction | n/a* | 9.2 | 99.1 | 100 | 100 | n/a = not applicable

EXAMPLE 8

Pathogen - *Cylindrocladium spathiphylli* - 81-118
Culture medium - potato dextrose agar
Spore Counts After Treatment With
Ethanolammonium Perbromide

|  | Water Control | 1 ppm | 5 ppm | 10 ppm | 25 ppm |
|---|---|---|---|---|---|
|  | 119 | 79 | 0 | 0 | 0 |
|  | 95 | 67 | 0 | 0 | 0 |
|  | 108 | 94 | 0 | 0 | 0 |
|  | 102 | 85 | 0 | 0 | 0 |
|  | 99 | 79 | 0 | 0 | 0 |
| average | 104.6 | 80.8 | 0 | 0 | 0 |
| average % reduction | n/a* | 22.8 | 100 | 100 | 100 | n/a = not applicable

EXAMPLE 9

In Vitro Test 9
Pathogen - *Corynespora cassiicola* - 88-34
Culture medium - potato dextrose agar
Spore Counts After Treatment With
Ethanolammonium Perbromide

|  | Water Control | 1 ppm | 5 ppm | 10 ppm | 25 ppm |
|---|---|---|---|---|---|
|  | 44 | 19 | 3 | 1 | 3 |
|  | 37 | 33 | 5 | 2 | 1 |
|  | 39 | 46 | 7 | 1 | 0 |
|  | 40 | 28 | 3 | 0 | 0 |
|  | 48 | 50 | 5 | 0 | 0 |
| average | 41.6 | 35.2 | 4.6 | 0.8 | 0.8 |
| average % reduction | n/a* | 15.4 | 88.9 | 98.0 | 98.0 | n/a = not applicable

EXAMPLE 10

In Vitro Test 10
Pathogen - *Alternaria panax* - 92-3
Culture medium - potato dextrose agar
Spore Counts After Treatment With
Ethanolammonium Perbromide

|  | Water Control | 1 ppm | 5 ppm | 10 ppm | 25 ppm |
|---|---|---|---|---|---|
|  | 4 | 9 | 0 | 0 | 2 |
|  | 6 | 7 | 4 | 3 | 2 |
|  | 0 | 4 | 2 | 4 | 1 |
|  | 1 | 6 | 3 | 7 | 0 |
|  | 0 | 4 | 3 | 1 | 0 |
| average | 2.2 | 6.0 | 2.4 | 3.0 | 1.0 |
| average % reduction | n/a* | 172.0 incr. | 9.0 incr. | 36.0 incr. | 54.5 decr. | n/a = not applicable
incr. = increase
decr. = decrease

Discussion of In Vitro Testing

The in vitro testing with ethanolammonium perbromide indicated that the compound worked effectively to kill the three bacteria tested. The compound was also effective on fungi, with near total kills for five of the six pathogens tested.

In summary, the results indicate that common plant pathogens are killed by exposure to 5–10 ppm Br from ethanolammonium perbromide. Accordingly, the efficacy of the present invention for the control of plant diseases is indicated by the in vitro tests.

EXAMPLES 11–15

Examples 11 through 15 relate to the in vivo testing of ethanolammonium perbromide with respect to its efficacy in controlling various pathogens. The test pathogens were applied to various plants in a research greenhouse and the plants were treated with varying amounts of ethanolammonium perbromide several days after infection. Pathogen counts were taken one to two weeks after treatment was initiated.

The results of the in vitro testing are shown in Examples 11–15 below.

EXAMPLE 11

| | Efficacy of Ethanolammonium Perbromide for Control of Alternaria Leaf Spot of Schefflera Brassaia Actinophylla. Number of Spots Given | | | | | | | | | | |
|---|---|---|---|---|---|---|---|---|---|---|---|
| | | | | | Day | | | | | | |
| Treatment | 1 | 2 | 3 | 4 | 5 | 6 | 7 | 8 | 9 | 10 | Mean |
| Water | 50 | 100 | 25 | 50 | 200 | 100 | 75 | 150 | 75 | 25 | 85.0 b |
| Compound A | 5 | 20 | 5 | 10 | 5 | 5 | 0 | 10 | 2 | 1 | 6.3 a |

Compound A = ethanolammonium perbromide
Treatment with approximately 15 to 25 ppm Compound A Significant control of Alternaria leaf spot was achieved with ethanolammonium perbromide in this test.

EXAMPLE 12

| | Efficacy of Ethanolammonium Perbromide for Control of Rhizoctonia Aerial Blight of Boston Fern Neprolepis Exaltata (Test Rhizoctonia-1). Percent of Plant Crown Infected | | | | | | | | | | |
|---|---|---|---|---|---|---|---|---|---|---|---|
| | | | | | Day | | | | | | |
| Treatment | 1 | 2 | 3 | 4 | 5 | 6 | 7 | 8 | 9 | 10 | Mean |
| Water | 75 | 100 | 50 | 100 | 90 | 100 | 90 | 100 | 90 | 100 | 89.5 c |
| Compound A | 75 | 50 | 50 | 50 | 30 | 80 | 80 | 50 | 75 | 75 | 61.5 b |

Compound A = ethanolammonium perbromide
Treatment with approximately 15 to 25 ppm Compound A Ethanolammonium perbromide provided significant disease control in this first trial on Rhizoctonia aerial blight of Boston Fern.

EXAMPLE 13

| | Efficacy of Ethanolammonium Perbromide for Control of Rhizoctonia Aerial Blight of Boston Fern Neprolepis Exaltata (Test Rhizoctonia-2). Percent of Plant Crown Infected | | | | | | | | | | |
|---|---|---|---|---|---|---|---|---|---|---|---|
| | | | | | Day | | | | | | |
| Treatment | 1 | 2 | 3 | 4 | 5 | 6 | 7 | 8 | 9 | 10 | Mean |
| Water | 50 | 50 | 25 | 40 | 20 | 5 | 20 | 25 | 15 | 30 | 28.0 c |
| Compound A | 30 | 15 | 30 | 25 | 15 | 10 | 10 | 5 | 15 | x | 17.2 b |

Compound A = ethanolammonium perbromide
Treatment with approximately 15 to 25 ppm Compound A Ethanolammonium perbromide provided significant disease control in this second trial on Rhizoctonia aerial blight of Boston Fern. 25 ppm Br appears to be a minimum for good control of Rhizoctonia aerial blight on Boston Fern.

EXAMPLE 14

Efficacy of Ethanolammonium Perbromide
for Control of Xanthomonas Leaf Spot
of English Ivy *Hedera Helix* (Test Ivy-1).
Number of Spots Given

| Treatment | Day | | | | | | | | | Mean |
|---|---|---|---|---|---|---|---|---|---|---|
| | 1 | 2 | 3 | 4 | 5 | 6 | 7 | 8 | 9 | |
| Water | 100 | 25 | 10 | 100 | 10 | x | 0 | 60 | 10 | 39.8 b |
| Compound A | 40 | 10 | 5 | 5 | 5 | 5 | 0 | 10 | 10 | 10.0 a |

Compound A = ethanolammonium perbromide
Treatment with approximately 15 to 25 ppm Compound A Ethanolammonium perbromide gave significant control of Xanthomonas leaf spot in this trial on English Ivy.

EXAMPLE 15

Efficacy of Ethanolammonium Perbromide
for Control of Xanthomonas Leaf Spot
of English Ivy *Hedera Helix* (Test Ivy-2).
Number of Spots Given

| Treatment | Day | | | | | | | | | Mean |
|---|---|---|---|---|---|---|---|---|---|---|
| | 1 | 2 | 3 | 4 | 5 | 6 | 7 | 8 | 9 | |
| Water | 35 | 15 | 20 | 10 | 25 | 30 | 20 | 5 | 5 | 18.3 b |
| Compound A | 8 | 5 | 5 | 3 | 15 | 15 | 0 | 25 | 10 | 9.6 a |

Compound A = ethanolammonium perbromide
Treatment with approximately 15 to 25 ppm Compound A Ethanolammonium perbromide gave significant control of Xanthomonas leaf spot in this trial on English Ivy.

Summary of In Vivo Testing

The results indicate that most of the pathogens were killed in vitro by exposure to 5–10 ppm Br from ethanolammonium perbromide. However, the results also indicated that higher rates are needed for in vivo versus vitro applications.

EXAMPLES 16–26

Plant pathogens are controlled by treatment with other water-soluble, mono- or di-substituted ammonium perhalides selected from the group consisting of propylammonium perbromide, diethanolammonium perbromide, butylammonium perbromide, methylethanolammonium perbromide, ethylethanolammonium perbromide, hexylammonium perbromide, octylammonium perbromide, dipropylammonium perbromide, dibutylammonium perbromide, diethylammonium perbromide, 1,6-hexanediammonium perbromide, and the corresponding chloro- and iodo-dibromides. The treatment is effective when the ammonium perhalide is provided as a solution in water, when applied in solid form in the plant environment, or when sprayed directly on the plant.

EXAMPLE 16

Schefflera is treated with a solution of propylammonium perbromide to determine the perhalide's efficacy in treating Alternaria Leaf Spot. Evaluation several days after treatment indicates that the plant disease is substantially controlled.

EXAMPLE 17

Boston fern is treated with a solution of diethanolammonium perbromide to determine the perhalide's efficacy in treating Rhizoctonia Aerial Blight. Evaluation several days after treatment indicates that the plant disease is substantially controlled.

EXAMPLE 18

English Ivy is treated with a solution of butylammonium perbromide to determine the perhalide's efficacy in treating Xanthomonas Leaf Spot. Evaluation several days after treatment indicates that the plant disease is substantially controlled.

EXAMPLE 19

Schefflera is treated with a solution of methylethanolammonium perbromide to determine the perhalide's efficacy in treating Alternaria Leaf Spot. Evaluation several days after treatment indicates that the plant disease is substantially controlled.

EXAMPLE 20

Boston fern is treated with a solution of ethylethanolammonium perbromide to determine the perhalide's efficacy in treating Rhizoctonia Aerial Blight. Evaluation several days after treatment indicates that the plant disease is substantially controlled.

EXAMPLE 21

English Ivy is treated with a solution of hexylammonium perbromide to determine the perhalide's efficacy in treating Xanthomonas Leaf Spot. Evaluation several days after treatment indicates that the plant disease is substantially controlled.

EXAMPLE 22

Schefflera is treated with a solution of octylammonium perbromide to determine the perhalide's efficacy in treating Alternaria Leaf Spot. Evaluation several days after treatment indicates that the plant disease is substantially controlled.

EXAMPLE 23

Boston fern is treated with a solution of dipropylammonium perbromide to determine the perhalide's efficacy in treating Rhizoctonia Aerial Blight. Evaluation several days after treatment indicates that the plant disease is substantially controlled.

EXAMPLE 24

English Ivy is treated with a solution of dibutylammonium perbromide to determine the perhalide's efficacy in treating Xanthomonas Leaf Spot. Evaluation several days after treatment indicates that the plant disease is substantially controlled.

EXAMPLE 25

Schefflera is treated with a solution of diethylammonium perbromide to determine the perhalide's efficacy in treating Alternaria Leaf Spot. Evaluation several days after treatment indicates that the plant disease is substantially controlled.

EXAMPLE 26

Boston fern is treated with a solution of 1,6-hexanediammonium perbromide to determine the perhalide's efficacy in treating Rhizoctonia Aerial Blight. Evaluation several gays after treatment indicates that the plant disease is substantially controlled.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for controlling diseases caused by living organisms in higher order plants, comprising applying to the roofs or leaves of the plant a water-soluble, mono- or di-substituted ammonium perhalide of the formula:

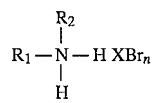

wherein;

$R_1$ and $R_2$ are independently hydrogen, hydroxyethyl, alkyl, cyclic alkyl, (alpha, omega)-alkyl, alkyl ether, polyoxyalkylene, polyether, heterocyclic ring-substituted alkyl or halogenated alkyl;

X is chlorine, bromine or iodine;

n is an integer of 2 through 6; and only one of $R_1$ and $R_2$ is hydrogen.

2. A method according to claim 1 wherein X is bromine.

3. A method according to claim 1 wherein the water-soluble, mono- or di-substituted ammonium perhalide is selected from the group consisting of ethanolammonium perbromide, propylammonium perbromide, diethanolammonium perbromide, butylammonium perbromide, methylethanolammonium perbromide, ethylethanolammonium perbromide, hexylammonium perbromide, octylammonium perbromide, dipropylammonium perbromide, dibutylammonium perbromide, diethylammonium perbromide, 1,6-hexanediammonium perbromide, and the corresponding chloro- and iodo-dibromides.

4. A method according to claim 2 wherein the water-soluble, mono- or di-substituted ammonium perhalide is ethanolammonium perbromide.

5. A method according to claim 1 wherein higher order plants are treated for disease control by incorporating ammonium perhalide into water to produce treated water having a concentration of ammonium perhalide sufficient to control selected diseases in plants, and contacting the higher order plants with the treated water.

6. A method as set forth in claim 5 wherein the plants are contacted with the treated water by means of spray irrigation.

7. A method as set forth in claim 1 wherein the ammonium perhalide is provided at a concentration of between about 10 ppm and about 200 ppm by weight in the treated water.

8. A method as set forth in claim 7 wherein the ammonium perhalide is provided at a concentration of between about 10 ppm and about 50 ppm by weight in the treated water.

9. A method as set forth in claim 8 wherein the ammonium perhalide is provided at a concentration of at least about 25 ppm by weight in the treated water.

10. A method as set forth in claim 9 wherein the ammonium perhalide provides a concentration of between about ppm and about 100 ppm bromine by weight in the treated water.

11. A method as set forth in claim 1 wherein the ammonium perhalide provides a concentration of between about ppm and about 25 ppm bromine by weight in the treated water.

12. A method as set forth in claim 5 wherein higher order plants are contacted with treated water by transporting water to the plants by water absorbent material, wherein the method includes the steps of:

arranging the plants and the water-absorbent material so that water may be transported through the water-absorbent material to contact the plants through the growth medium in which they are rooted;

incorporating ammonium perhalide into water to produce treated water having a concentration of ammonium perhalide sufficient to control selected diseases in plants; and delivering said treated water to said water absorbent material, thereby effecting transport of treated water to said plants or said growth medium.

13. A method as set forth in claim 12 wherein the ammonium perhalide comprises ethanolammonium perbromide.

14. A method as set forth in claim 1 wherein the ammonium perhalide is applied to a growth medium in which the plant is rooted, the ammonium perhalide being dissolved in, and conveyed to the rhizosphere by precipitation or irrigation water received by said growth medium.

15. A method as set forth in claim 14 wherein the ammonium perhalide comprises ethanolammonium perbromide.

16. A method as set forth in claim 1 wherein higher order plants are harvested, the method including:

contacting growing higher order plants with the ammonium perhalide; and harvesting said growing plants to collect harvested plants, whereby rotting or spoiling of the harvested plants is inhibited.

17. A method as set forth in claim 15 wherein the ammonium perhalide comprises ethanolammonium perbromide.

18. A method as set forth in claim 1 wherein higher order plants are treated with ammonium perhalide and harvested fruit or seeds are produced from the treated plants, the method including the steps of:

contacting growing higher order plants bearing fruit or seeds with the ammonium perhalide;

harvesting fruit or seeds from higher order plants to collect harvested fruit or seeds, whereby rotting or spoiling of the harvested fruit or seeds is inhibited.

19. A method as set forth in claim 17 wherein the ammonium perhalide comprises ethanolammonium perbromide.

20. A method as set forth in claim 1 wherein the ammonium perhalide is applied to a growth medium in which a seed or bulb for the plant is implanted, the ammonium perhalide being dissolved in and conveyed by precipitation or irrigation water received by said growth medium to said seed, bulb, or plant resulting from germination of said seed or bulb.

21. A method as set forth in claim 19 wherein the ammonium perhalide comprises ethanolammonium perbromide.

22. A method for controlling diseases caused by living organisms in higher order plants, comprising applying to the roots or leaves of the plant a stabilized, aqueous perhalide composition comprising:

(a) a water solution of an ammonium hydrohalide of the formula:

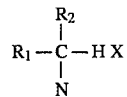

wherein:

$R_1$ and $R_2$ are independently hydrogen, hydroxyethyl, alkyl, cyclic alkyl, (alpha, omega)-alkyl, alkyl ether, polyoxyalkylene, polyester, heterocyclic ring-substituted alkyl or halogenated alkyl;

X is chlorine, bromine or iodine; and only one of $R_1$ and $R_2$ is hydrogen; and (b) bromine, wherein the molar ration of hydrohalide to bromine is between about 2:1 and about 4:1.

23. A method according to claim 21 wherein a portion of the ammonium hydrohalide is replaced with a stabilizing salt selected from the group consisting of alkali metal bromides and ammonium bromide.

24. A method as set forth in claim 21 wherein the ammonium perhalide comprises ethanolammonium perbromide.

* * * * *

UNITED STATES PATENT AND TRADEMARK OFFICE
CERTIFICATE OF CORRECTION

PATENT NO. : 5,461,077
DATED : October 24, 1995
INVENTOR(S) : Dennis M. Borden; Nicolai A. Favstritsky It is certified that error appears in the above-indentified patent and that said Letters Patent is hereby corrected as shown below:

In column 5, line 1, please change "to" to --do--.

In column 16, line 3, please insert --5-- before "ppm".(first occurrence)

In column 16, line 7, please insert --5-- before "ppm".(first occurrence)

In column 17, line 10, change "C" in the formula to --N--.

In column 17, line 12, change "N" in the formula to --H--.

Signed and Sealed this

Twenty-third Day of January, 1996

*Attest:*

BRUCE LEHMAN

*Attesting Officer*     *Commissioner of Patents and Trademarks*